(12) United States Patent  (10) Patent No.: US 12,376,908 B2
Zhang et al.  (45) Date of Patent: Aug. 5, 2025

(54) TRACTION DEVICE FOR CURVED BALLOON CATHETER AND TRACTION METHOD

(71) Applicant: Shanghai Techbank Medical Technology Co., LTD., Shanghai (CN)

(72) Inventors: Chuanhai Zhang, Shanghai (CN); Subbakrishna Shankar, Shaker Hts, OH (US); Fanqi Li, Shanghai (CN)

(73) Assignee: SHANGHAI TECHBANK MEDICAL TECHNOLOGY CO., LTD, Shanghai (CN)

( * ) Notice: Subject to any disclaimer, the term of this patent is extended or adjusted under 35 U.S.C. 154(b) by 1044 days.

(21) Appl. No.: 16/757,262

(22) PCT Filed: Aug. 30, 2018

(86) PCT No.: PCT/CN2018/103280
§ 371 (c)(1),
(2) Date: Apr. 17, 2020

(87) PCT Pub. No.: WO2019/072047
PCT Pub. Date: Apr. 18, 2019

(65) Prior Publication Data
US 2021/0186621 A1  Jun. 24, 2021

(30) Foreign Application Priority Data
Oct. 10, 2017 (CN) .......................... 201710938901.9

(51) Int. Cl.
*A61B 34/20* (2016.01)
*A61B 17/02* (2006.01)
(Continued)

(52) U.S. Cl.
CPC .............. *A61B 34/20* (2016.02); *A61B 17/02* (2013.01); *A61M 25/0026* (2013.01);
(Continued)

(58) Field of Classification Search
CPC ... A61B 2090/3933; A61B 2090/3966; A61M 31/005
See application file for complete search history.

(56) References Cited

U.S. PATENT DOCUMENTS 4,763,654 A  8/1988 Jang
D303,288 S  9/1989 Harboe
(Continued)

FOREIGN PATENT DOCUMENTS

CN  103055411 A  4/2013
CN  103442650 A  9/2013
(Continued)

*Primary Examiner* — Amelie R Davis

(57) ABSTRACT

Provided is a traction device for curved balloon catheter, which is characterized by comprising: a catheter (5) with a handle (2) at one end, a locator (3) and a traction balloon (4) arranged outside the catheter (5), which one or more cavities are arranged in the catheter (5), the catheter part is provided with at least one hole, at least one cavity fills and discharges the traction balloon (4) with fluid through the hole, the traction balloon (4) bends to one side when filled with fluid, and the handle (2) can drive the catheter (5) and the traction balloon (4) to rotate, thus realizing a simple and reliable traction.

9 Claims, 3 Drawing Sheets

(51) Int. Cl.
*A61B 90/00* (2016.01)
*A61M 25/00* (2006.01)
*A61M 25/10* (2013.01)
*A61M 31/00* (2006.01)

(52) U.S. Cl.
CPC ...... *A61M 25/1011* (2013.01); *A61M 31/005* (2013.01); *A61B 2034/2065* (2016.02); *A61B 2090/3966* (2016.02); *A61M 2025/0008* (2013.01); *A61M 2210/105* (2013.01)

(56) References Cited

U.S. PATENT DOCUMENTS

| | | | |
|---|---|---|---|
| 4,862,886 | A | 9/1989 | Clarke |
| 5,147,377 | A | 9/1992 | Sahota |
| 5,400,770 | A * | 3/1995 | Nakao ............... A61B 17/00234 606/116 |
| D360,260 | S | 7/1995 | Brandt |
| D390,659 | S | 2/1998 | Chan |
| 8,795,312 | B2 | 8/2014 | Fan et al. |
| 9,439,705 | B2 | 9/2016 | Fan et al. |
| D851,245 | S | 6/2019 | Baxter |
| 10,463,468 | B2 | 11/2019 | Janardhan |
| D879,958 | S | 3/2020 | Medical |
| 2002/0165537 | A1 | 11/2002 | Kelley |
| 2006/0085022 | A1 | 4/2006 | Hayes |
| 2008/0306583 | A1 | 12/2008 | Bashiri |
| 2008/0312589 | A1 | 12/2008 | Dlugos |
| 2012/0053566 | A1 * | 3/2012 | Tada ................ A61B 17/00491 604/514 |
| 2012/0150210 | A1 | 6/2012 | Fan et al. |
| 2014/0012304 | A1 | 1/2014 | Lampropoulos |
| 2014/0243580 | A1 | 8/2014 | Isham |
| 2014/0243875 | A1 | 8/2014 | Chen |
| 2014/0277062 | A1 | 9/2014 | Pepper |
| 2014/0309646 | A1 | 10/2014 | Fan et al. |
| 2015/0202089 | A1 | 7/2015 | Campbell |
| 2015/0342590 | A1 | 12/2015 | Cantillon-Murphy et al. |
| 2017/0150957 | A9 | 6/2017 | O'Shea et al. |
| 2017/0252027 | A1 | 9/2017 | Kasic |
| 2018/0296264 | A1 * | 10/2018 | DeSimone ......... A61B 18/1492 |

FOREIGN PATENT DOCUMENTS

| | | |
|---|---|---|
| CN | 104189989 A | 12/2014 |
| CN | 201333252 Y | 8/2015 |
| CN | 204581372 U | 8/2015 |
| CN | 2120592 U | 9/2015 |
| CN | 104921853 A | 9/2015 |
| CN | 105997161 A | 10/2016 |
| CN | 106422038 A | 2/2017 |
| CN | 304614456 | 5/2018 |
| CN | 305072250 | 3/2019 |
| EP | 0521595 A2 | 1/1993 |
| JP | D1637001 | 7/2019 |
| WO | WO 2014096370 A2 | 6/2014 |
| WO | WO216160589 A1 | 10/2016 |
| WO | WO2017/004432 A1 | 1/2017 |
| WO | WO2017/049313 A1 | 3/2017 |

* cited by examiner

TRACTION DEVICE FOR CURVED BALLOON CATHETER AND TRACTION METHOD

TECHNICAL FIELD

The invention relates to a catheter retractor, in particular to a bending balloon catheter retractor device and a pulling method thereof

BACKGROUND OF THE INVENTION

The retractor is also referred to as a pull hook to pull the tissue, reveal a desired surgical range, facilitate exploration and operation, and can be divided into two types of hand-held pull hooks and automatic hooks. There are a variety of different shapes and sizes of specifications that can be selected depending on the needs of the procedure.

Conventional retractors require a larger operating space, which requires a larger surgical wound. Meanwhile, a traditional retractor is made of a plurality of metals, meanwhile, a sharp end is provided, secondary trauma of the patient is easily caused, and important organ tissues are damaged.

Current retractable tissue retractors are increasingly being widely used, which can pass through the working chamber of a retractable endoscope. Tissue retractors are used in endoscopic and open surgery, including scalable endoscopic, laparoscopic, and common surgical procedures. In order to accommodate specific requirements in surgical procedures, the length and diameter of such a tissue retractor can be constant or variable. A retractable endoscopic tissue retractor can be used to secure the organ tissue, thereby pulling and operating it in some manner.

The catheter retractor is used for tissue traction in surgery, which completes the pulling operation through natural lumen intervention or open surgical intervention. Procedures include, but are not limited to, various laparoscopic procedures, cardiovascular major surgery, brain surgery, digestive tract surgery, urinary disorder surgery, etc. including, but not limited to, gastrointestinal tract, esophagus, airway, urethra, vagina, bladder, and the like. Distraction objectives include, but are not limited to, protecting a particular tissue, removing a particular tissue to facilitate a surgical procedure.

The expansion deformation of the capsule enables the gap between the tissues to be a better practice of a metal puller, the volume is small, and the part of the human tissue needing to be isolated can be placed on the premise that the tissue of the human body is not excessively damaged. Meanwhile, the surface of the inflated balloon is smooth and soft, and damage to human tissues is not easily caused. For example, Chinese Patent 200580028684.5 provides a tissue removal/separation device. The device includes a balloon that can expand between a first tissue and a second tissue of the body. The balloon has an expanded shape that is selected to be capable of removing or separating the first tissue from the second tissue in a manner suitable to protect the first tissue from application therapy to the second tissue.

However, this invention is merely illustrative of the possibility of using balloon inflation to isolate human tissue, and an original inflation balloon is not suitable for expansion isolation in any human tissue. The use of such a balloon, even to some extent, poses a significant potential risk to the inflation of the human body. Moreover, the balloon can be tightly attached to the tissue of the human body at a certain pressure, although it is more difficult to isolate the different tissues while also tightly packing the limited space between the two, and the balloon also has the risk of bursting if the balloon is passed through the sharp surgical device and the burning surgical means. Therefore, compared with a mechanical retractor, the balloon expansion device can not effectively realize large-displacement distraction and does not occupy a surgical space, and can only play the role of isolating human tissue. In addition, it is also difficult to determine where the balloon is specifically located from the outside of the body, while generally such procedures are generally quite sophisticated. At the same time, the in-vivo effusion is also more difficult to exclude, resulting in a new increase risk.

Accordingly, there is a need for a surgical device that utilizes a balloon as a retractor that is more sophisticated and that is suitable for practical situations of human surgery to combine the advantages of both balloon inflation and mechanical retraction.

SUMMARY OF THE INVENTION

The invention aims to provide a bending balloon catheter distraction device for natural lumen intervention or open surgical intervention based on the problems, solves the problem that the current catheter retractor and the balloon isolation device are not high in precision and reliability and cannot adapt to human surgery, thereby realizing a simple and reliable catheter distraction.

In order to achieve the above object, the invention provides a bending balloon catheter distraction device, which comprises a catheter with a handle at one end, a positioner or positioner balloon and a traction bag, also referenced herein as a balloon, traction balloon, traction bladder, pulling bag, pulling balloon or pulling bladder, are arranged outside the catheter, wherein one or more lumina are formed in the catheter, at least one hole is formed in the catheter portion, at least one lumen is used for fluid filling the traction bag through the hole, and when the pulling balloon or traction bag is filled with fluid, one side is bent, and the handle can drive the catheter and the pulling balloon or traction bag to rotate.

Where the positioner balloon may be a device that employs a developer, its position in the body may then be viewed by X-ray. The positioner is one or more balloon or balloons positioned at a fixed position of the catheter, and the positioner balloon is filled with fluid and can clamp the lumen tube in the human body. The handle includes a portion that is held stationary, and a rotatable angle portion. The handle is provided with a mark indicating the angle, and when the handle is rotated, the relative azimuth angle of the pulling balloon is marked. The catheter is made of material which is not easy to self-twist; and when the catheter is left on the outer part of the human body cavity to rotate, the pulling balloon is rotated by a certain proportion at the same time. A length of scale on the catheter is used to mark the depth of insertion of the catheter. One or more of the lumina are used to inflate the balloon. At least one of the lumina is used for drainage of the effusion. The lumen for the drainage effusion is located at the upper end of the pulling balloon at an open position on the catheter. At least one of the lumina is used for spraying the developer; the hole or aperture for spraying of the developer is located at the upper end of the pulling balloon. At least one of the lumina is used for absorbing negative pressure, the open position of the lumen is located between the two ends of the balloon, and the holes used for absorbing the negative pressure can be provided as one or more. The pulling balloon can be made of a raw material mixed with a developer and has the function of fully developing under the X-ray. The pulling balloon is used for pulling the esophagus. The pulling balloon is located between the second stenosis and the third stenosis of the esophagus, and the diameter of the balloon after filling with the fluid is larger than the diameter of the esophagus at the stenosis.

Another object of the present invention is to provide a curved balloon catheter retractor for use with the esophagus of a patient during a cardiac ablation procedure. The present invention provides a curved balloon catheter retractor comprising a handle, a multi-lumen catheter, two positioner balloons, and a middle pulling balloon. The three lumina in the multi-lumen catheter are respectively provided with holes at the positions where the three balloons are located and are used for respectively filling the three balloons with fluid. The two positioner balloons are located at the two ends of the middle pulling balloon and are respectively clamped with the esophagus for fixation; when the pulling balloon is filled with fluid, the esophagus is bend to drive the esophagus to bend, so that the esophagus is pulled away from the original position.

The positions of the four lumina are respectively a large lumen in the middle and a plurality of small lumina around the large lumen; each small lumen is provided with a hole at the position where each capsule or balloon is locate and is used for respectively inflating the capsule; and the middle of the lumen is provided with a hole at the upper end of the upper end of the balloon for drainage of saliva. The other lumen is in communication with the opening between the positioner balloon and the pulling balloon, and is used for pumping gas to the esophagus pulling balloon. Still another lumen may be used to spray a developer to the inner wall of the esophagus for displaying esophageal bending conditions.

It is yet another object of the present invention to provide a safe and effective method of retracting a balloon catheter. In order to achieve the aim of the invention, the invention provides a method for pulling a curved balloon catheter, which is characterized by comprising the following steps: inserting an uninflated fluid bending balloon catheter into a human body lumen needing to be pulled; monitoring whether the balloon reaches a predetermined position; filling the positioner balloon with the fluid to enable the balloon catheter to be clamped in the human body lumen; and filling the pulling balloon with fluid so that the balloon catheter is bent to achieve the purpose of bending and pulling the human body lumen."

After the balloon is filled with fluid, the invention further comprises a step of pumping the fluid by utilizing the lumen of the suction pressure, and then the pulling balloon is distracted, so that the purpose of bending the lumen is achieved.

Yet another object of the present invention is to provide a curved balloon catheter retraction method for esophageal retractor, comprising the steps of: inserting a balloon catheter from the oral cavity or nasal cavity into the esophagus, opening the distal balloon when the distal balloon enters between the second stenosis and the third stenosis, and continuing to push to the third stenosis; The upper end of the balloon is opened, and the balloon is clamped under the second stenosis; then, the relative position of the bending direction and the heart is determined through the marking on the catheter and the handle, the middle pulling balloon is distracted, the esophagus is driven to bend, and the esophagus is driven to bend away from the heart or the cardiac surgery position.

When the position of the pulling balloon needs to be moved in the using process, the catheter and the capsule are driven to rotate through the rotating handle, so that the esophagus is driven to rotate, so that the tissue or the position needing to be avoided in the surgery is avoided all the time. When the balloon is used for esophageal pulling, the balloon is located between the second stenosis and the third stenosis of the esophagus, and the diameter of the balloon inflated with the fluid is greater than the diameter of the esophagus at the stenosis. When in use, the balloon bag is filled with the fluid, the lumen of the negative pressure is used for pumping gas, and finally the pulling balloon is expanded, so that the purpose of bending the esophagus is achieved.

The device has the beneficial effects that a better instrument is provided for tissue pulling, and compared with an existing tissue pulling mode, the device is better in controllability, safer to use and more comfortable to patients; in a specific manner, such as for esophageal pulling, an existing oral placement instrument can be changed into nasal placement, and the operability is better; and the use of the balloon and the rotary scales enables the pulling operation (acting position and pulling orientation).) More precision is achieved; the cavity and the opening are increased, and the operation of more practicability such as saliva drainage, spraying developer, suction pressure and the like is realized.

DETAILED DESCRIPTION OF THE PREFERRED EMBODIMENTS

Figure 1:
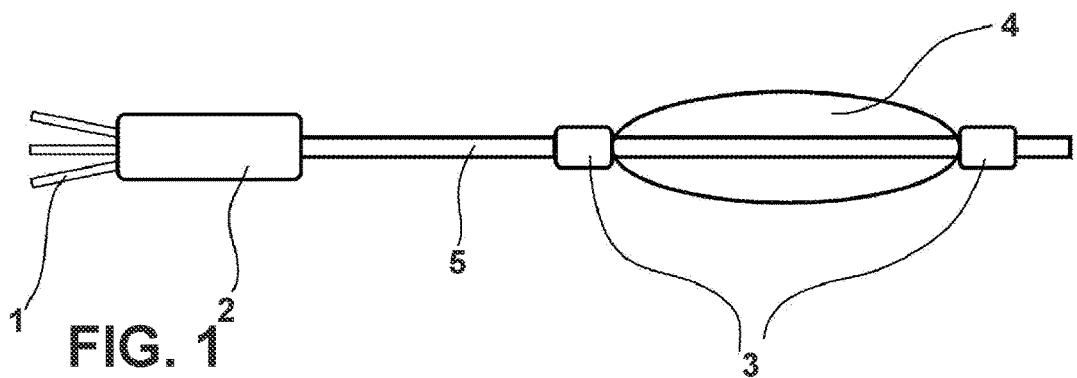
FIG. 1 is a schematic view of the structure of the present invention.

The invention will be described in further detail below in conjunction with the appended drawings and examples:

Please refer to FIG. 1, which is a schematic view of the structure of the present invention. As shown in FIG. 1, A curved balloon catheter retractor of the present invention, The following parts were made up: One end has a flow guide tube and a handle 2 of valve 1, A positioner 3 and a pulling balloon 4 are arranged outside the catheter 5, one or more lumina are formed in the catheter 5, at least one hole is formed in the portion of the catheter 5 in the positioner 3, the at least one lumen is provided with at least one hole through the flow guiding pipe and the valve 1, the at least one lumen is filled with fluid through the hole to the positioner 3 and the pulling balloon 4, and the fluid is generally a liquid and a gas which is bent towards one side when the pulling balloon 4 is filled with fluid. In one embodiment, the gas is injected into the intake port by a syringe. Closing the flow guide tube and valve 1 after injecting the gas may cause the pulling balloon 4 to hold the gas pressure. In general, the pulling balloon 4 is located near the middle or the end of the catheter 5, and the upper and lower ends of the pulling balloon 4 are closed on the catheter 5 by laser welding or bonding. The advantage of using laser welding is that the pulling requires a large pressure inside the capsule to create sufficient rigidity, sometimes up to 10 atmospheres, with only laser welding ensuring reliable sealing. The pulling balloon 4 material of the present invention is semi-compliant or non-compliant, that is, within a larger pressure range, the change in volume and profile after expansion of the pulling balloon 4 is small, thereby protecting the organ from excessive extrusion. The positioner 3 can be two compliant balloon balloons 3 which are respectively fixedly arranged on the catheter 5 at the two ends of the pulling balloon 4 The balloon 3, in some embodiments, is one or more, when one, can be placed at the proximal or distal end of the retractor balloon 4. Balloon 3 is a compliant balloon or non-compliant balloon, which is relatively small in length. Where the number of balloon 3 is multiple, some of the balloon inflation fluid (gas or liquid) may be selected as well during use. The pulling balloon 4 is a non-compliant balloon, and the length-diameter is relatively large. The balloon 3 and the pulling balloon 4 can be made from a raw material mixed with a developer so that it has the function of being fully developed under X-rays.

Figure 2:
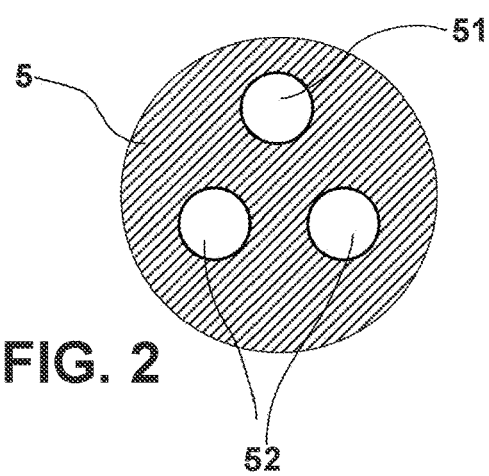
FIG. 2 is a cross-sectional view of a catheter portion of the present invention.

Please refer to FIG. 2, which is a cross-sectional view of a catheter portion of the present invention. In FIG. 2, the cross-section of the catheter 5 has three lumina, two of which are used to inflate the balloon 3, and the other lumen 51 is for inflating the balloon 4

Figure 3:
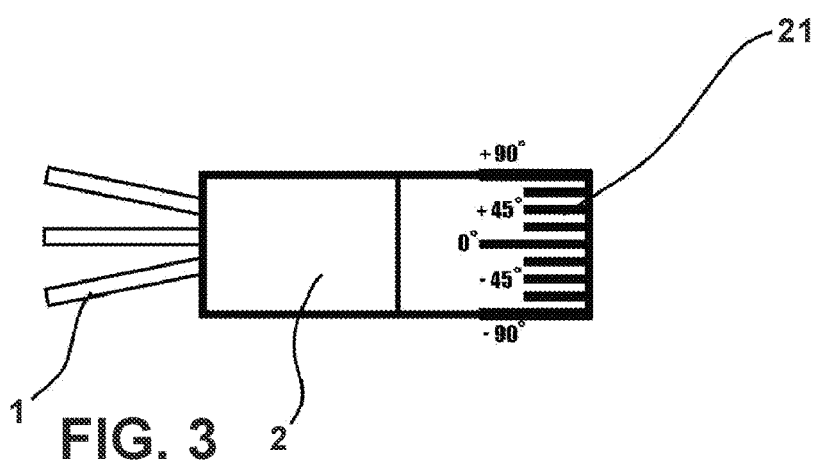
FIG. 3 is a schematic view of a handle portion of the present invention.
Figure 4:
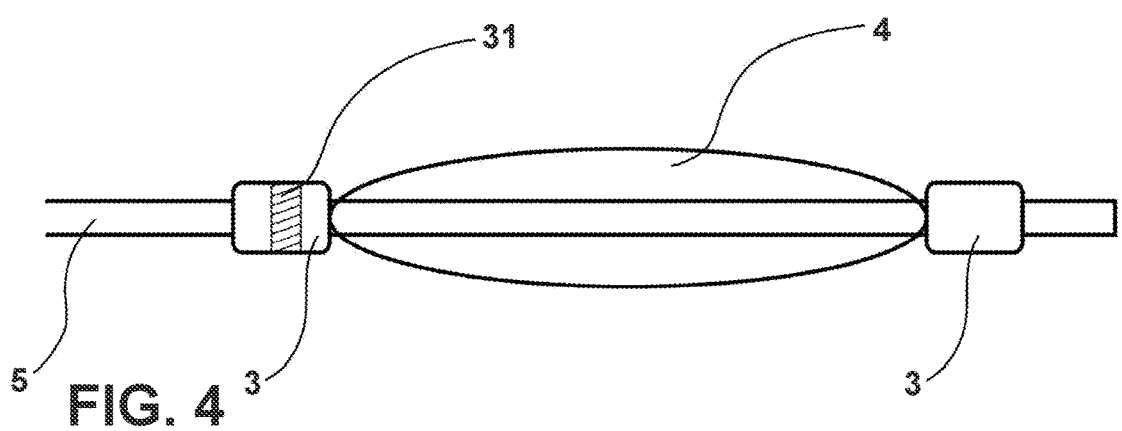
FIG. 4 is a schematic diagram of one embodiment of the present invention.

FIG. 3 is a schematic view of a handle portion of the present invention. The handle 2 is used for inflating, injecting, holding, rotating and the like. The inflation and/or injection port 1, determined according to a particular design, has one or more. The handle 2 includes a portion that is held stationary, and a rotatable angle. The handle 2 has a graduated scale 21 on the handle 2 which, when rotated, is used to mark the relative angular orientation of the pulling bladder relative to the organ of the human body or where the tissue needs to be pulled Please refer to FIG. 4, which is a schematic diagram of one embodiment of the present invention. In FIG. 4, the positioner or balloon 3 has a positioning mark 31, which may be a developing material, such as a barium sulfate contrast agent. Other positioning devices such as infrared or radio frequency (RF) tags or the like can also be used to enable the physician to measure the specific location of the positioner or balloon 3 in the body outside of the patient's body. In some embodiments, the catheter 5 has a developed line on the catheter 5 for development as X-rays.

Figure 5:
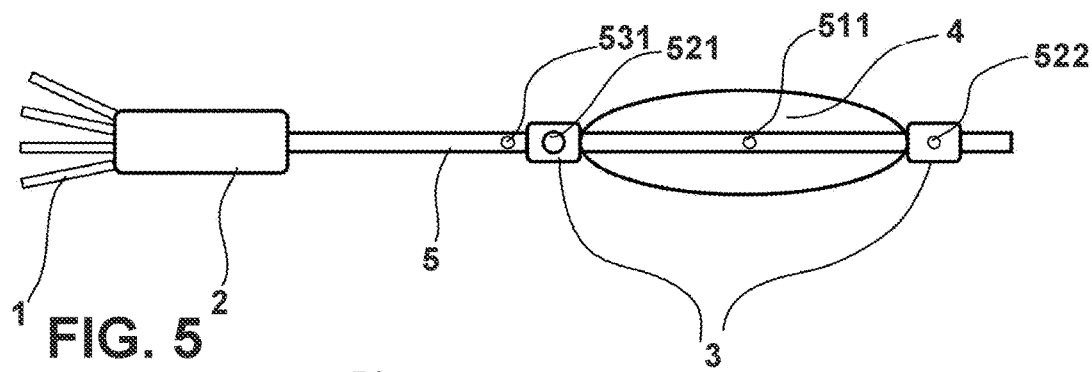
FIG. 5 is a schematic diagram of another embodiment of the present invention.
Figure 6:
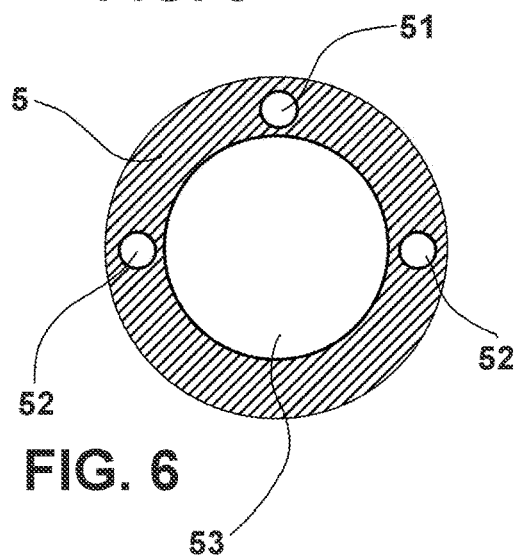
FIG. 6 is a cross-sectional view of the catheter portion of the embodiment of FIG. 5.

Please refer to FIG. 5 and FIG. 6, which are schematic diagrams of another embodiment of the present invention. FIG. 6 is a cross-sectional view of the catheter portion of the embodiment of FIG. 5. The balloon catheter retractor includes a handle 2, a four-lumen catheter 5, two compliant balloon balloons 3, a semi-compliant or non-compliant pulling balloon 4 with four lumina, respectively, an intermediate large lumen 53, and surrounding three small lumina 51 and 52; three small lumina are provided with holes 511, 521, 522 at the three bladders, respectively, for inflating the three bladders, respectively. The intermediate larger lumen 53 opens up the upper opening 531 of the balloon at the upper end for drainage of saliva.

The catheter 5 is a hollow catheter with one or more lumina inside the catheter 5. At least one lumen 51 in the lumen is dedicated to filling the pulling bladder 4 with fluid. One or more of the lumina are used to inflate the balloon 3. At least a lumen 53 in the lumen has a lumen 53 for draining saliva; the lumen 53 of the drainage saliva is located at the upper end of the pulling balloon 4 at the location of the opening 531 on the catheter 5; if the balloon 3 is provided, the upper end of the balloon 3 is located at the upper end of the balloon 3

Figure 7:
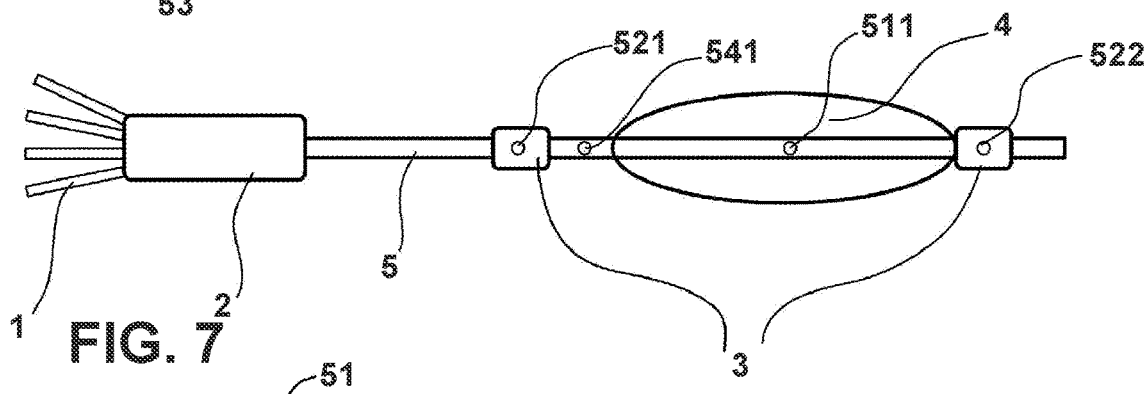
FIG. 7 is a schematic view of yet another embodiment of the present invention.
Figure 8:
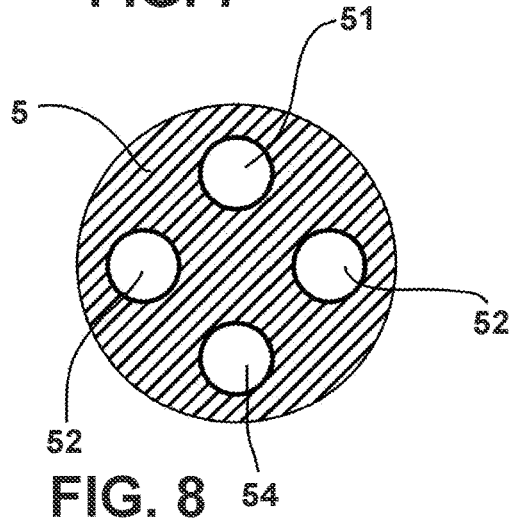
FIG. 8 is a cross-sectional view of the catheter portion of the embodiment of FIG. 7.

Please refer to FIGS. 7 and 8, which are schematic diagrams of yet another embodiment of the present invention. FIG. 8 is a cross-sectional view of the catheter portion of the embodiment of FIG. 7. Unlike the previous embodiment, there is no apparent size of the lumen in the present embodiment. The three lumina 51 and 52 of the four-lumen catheter 5 are open at the locations of the three balloons, respectively, to inflate the three balloons, respectively. Another lumen 54 is used to spray a developer (meal; barium sulfate); the hole 541 of the developer is located at the upper end of the pulling balloon 4; as with the balloon 3, between the pulling balloon 4 and the upper balloon 3. The effect of the spray developer is to enable the inner wall of the esophagus to develop, clearly knowing the distance of the distraction.

In other embodiments, the lumen 54 is used to suction a negative pressure, the open position of which is located in the middle of the two balloon 3, and the holes used to suction the negative pressure may have one or more. In particular, the balloon 3 is inflated first, then air is drawn through the lumen 54 with negative pressure, and finally the pulling balloon 4 is distracted, so that the purpose of bending the esophagus is achieved.

The catheter is made of a material which is not easy to twist; when the catheter is left outside the human body cavity, a certain proportion of angle is rotated at the same time. At the same time, there is a length of scale on the catheter to mark the depth of catheter insertion.

The invention also provides a pulling method, which can be inserted into a single-lumen/multi-lumen catheter pipeline in an animal body and can be expanded into an arc-shaped pulling balloon after being injected into the fluid, the pulling balloon is linked to the outside of the catheter, and the catheter can be offset towards the protruding direction of the pulling balloon and can be combined with an operating handle and other related accessories. Tissue traction for use in surgery is accomplished by either natural lumen intervention or open surgical intervention. Procedures include, but are not limited to, various laparoscopic procedures, cardiovascular major surgery, brain surgery, digestive tract surgery, urinary disease surgery, and the like. The retractor tissue includes, but is not limited to, the gastrointestinal tract, the esophagus, the airway, the urethra, the vagina, the bladder, and the like. Distraction objectives include, but are not limited to, protecting a particular tissue, removing a particular tissue to facilitate a surgical procedure.

The curved balloon catheter of the retractor is regulated by a handle to be inserted into the body through a human body natural cavity or a surgical mode. The position and angle of rotation of the catheter can be adjusted with the handle with the aid of an image device to lock the position and angle with the handle. Inflation of the balloon may be accomplished by an insufflation port of the handle attachment or any other insufflation pathway. After the balloon is inflated, the balloon is inflated and exhibits a curved shape, at least one section of the catheter pipeline has at least one section of bending, and the bending part of the final balloon catheter can complete the pulling or shifting effect of the tissue.

Figure 9:
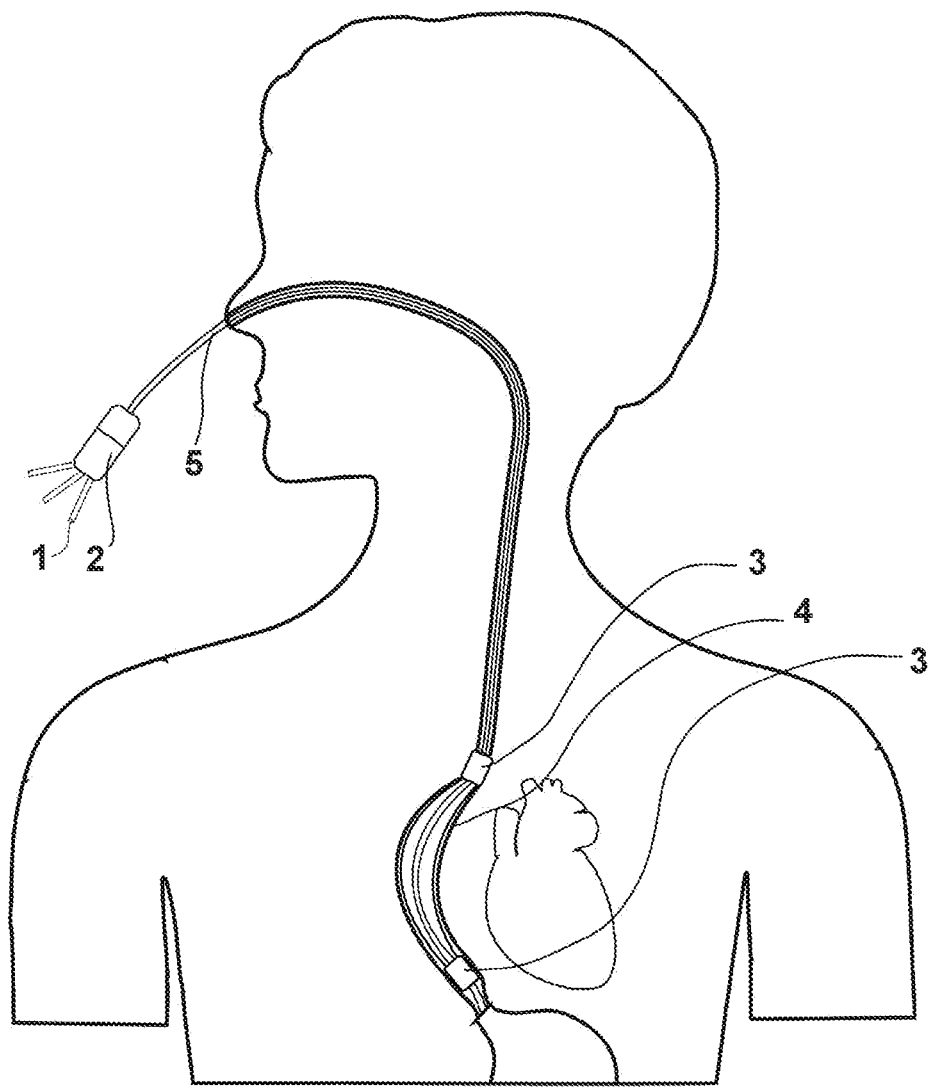
FIG. 9 is a schematic drawing of a curved balloon catheter distraction device retractor.

The effect of the catheter retractor is described in terms of atrial fibrillation ablation complications. Atrial fibrillation is the most common arrhythmia, while atrial fibrillation radiofrequency (RF) ablation therapy has been gradually recognized in recent years as a better solution than drug therapy and conventional surgical procedures. The occurrence of atrial esophageal fistula complications arises from the spatial relationship between the left atrium and the esophagus. Since the esophagus is at the posterior mediastinum, the posterior wall of the left atrium is separated from the posterior wall of the left atrium by only the pericardial oblique sinus, while the posterior wall of the left atrium and the anterior wall of the esophagus are both thin, and high temperature and high energy in the ablation procedure is likely to cause excessive damage to the esophagus. Atrial esophageal fistula complications have extremely high mortality, in order for the surgical safety to be drawn away from the heart, FIG. 9 is a schematic diagram of a curved balloon catheter retractor pulling on the esophagus. In FIG. 9, a catheter which is externally provided with a balloon is inserted into a patient's natural or surgical forming cavity, the balloon portion is inserted into the cavity position needing to be pulled, the catheter is inflated to inflate the balloon, the balloon is bent to bend towards one side after inflation of the balloon, the catheter is bent and causes the patient cavity to bend, and the distraction displacement is achieved.

When in use, the catheter 5 is inserted into the esophagus from the nasal cavity, when the distal balloon 3 enters between the second stenosis and the third stenosis of the esophagus, the distal balloon 3 is opened, and the balloon 3 continues to be pushed to the third stenosis; the upper end of the balloon 3 is opened, and the balloon 3 is clamped under the second stenosis; and then the middle pulling balloon 4 is opened to bend, and the esophagus is driven to bend. During use, the catheter 5 and balloon 3, 4 are driven to rotate by rotating the handle 2 so that the esophagus changes in the direction of deflection in the body, thereby always avoiding ablation points of the ablation of the heart. After the balloon 3 is opened, the esophagus is pumped by using the opening, and after a certain negative pressure range is reached, the pulling balloon 4 is distracted, so that the purpose of bending the esophagus is achieved. The aperture can also be used to spray a developer such that the esophageal curved portion can be developed under X-rays.

In particular, when used for esophagus pulling, the catheter is inserted into the esophagus through the nasal cavity or the oral cavity, after the catheter reaches the position, the relative position of the bending direction and the heart is determined through marking on the catheter and the handle, then the pulling balloon is inflated and distracted, and the esophagus is pulled by using the pulling balloon; and when the positioning of the pulling balloon needs to be rotated and adjusted in the horizontal section (cardiac ablation is needed to replace the ablation point)) By rotating the whole catheter through the knob device on the handle, the pulling balloon is driven to rotate, so that the esophagus is pulled away from the new ablation point in the new direction. The pulling balloon is positioned between the second stenosis and the third stenosis of the esophagus when the esophagus is pulled, the diameter of the balloon is larger than the diameter of the esophagus of the stenosis, the length of the pulling balloon is 10-15 cm, the working air pressure is 2-8 atm, and the pulling distance is 2-4 cm.

Those skilled in the art will also appreciate that other variations can be made within the spirit and scope of the present invention, and that various modifications that are derived in accordance with the spirit of the invention should still be within the scope of the invention.

The invention claimed is:

1. A curved balloon catheter retractor device comprising:
a catheter with a handle at one end,
an inflatable positioner positioned at a fixed location on the catheter, and
a pulling balloon arranged outside the catheter adjacent the inflatable positioner and with upper and lower ends thereof being sealed on the catheter by laser welding or bonding,
wherein a plurality of lumens are formed in the catheter, and at least one first hole is formed in the catheter, at least one first lumen of the plurality of lumens is adapted to fill the pulling balloon with fluid through the at least one first hole of the catheter, and when the pulling balloon is filled with fluid, one side exhibits a curved shape;
and wherein at least one second lumen of the plurality of lumens in the catheter, which at least one second lumen is not in fluid communication with the at least one first lumen of the pulling balloon, can be used for drainage in an esophagus through an upper opening at a proximal end of the catheter,
and wherein the catheter is configured to bend when the pulling balloon is filled with fluid to form a curved shape;
and the handle is configured to drive the catheter and the pulling balloon to rotate,
wherein the handle comprises a portion that may be held stationary and a rotatable angle portion provided with an angular dimension indicated thereon, and when the handle is rotated, the handle is configured to be used to mark the relative azimuthal angle of the pulling balloon.

2. The curved balloon catheter retractor device of claim 1, wherein said inflatable positioner is an inflatable positioner balloon comprised of a radiopaque material configured for viewing the position of the positioner balloon under X-ray.

3. The curved balloon catheter retractor device of claim 1, wherein the inflatable positioner is one or more balloons positioned at a fixed location on the catheter, the one or more balloons adapted to be filled with fluid.

4. The curved balloon catheter retractor device of claim 1, wherein the catheter is made of a material that is not susceptible to self-twisting, and rotation of the catheter handle also rotates the pulling balloon.

5. The curved balloon catheter retractor device of claim 4, wherein the length of the pulling balloon is 10 to 15 cm.

6. The curved balloon catheter retractor device of claim 1, wherein the catheter has a length of scale for marking insertion of the catheter.

7. The curved balloon catheter retractor device of claim 1, wherein at least one of said plurality of lumens is adapted to spray a developer, and an aperture for spraying of the developer is located on the proximal end of the catheter at an upper end of the pulling balloon, and between the pulling balloon and the positioner.

8. The curved balloon catheter retractor device of claim 1, wherein at least one of said plurality of lumens is adapted for receiving a negative pressure.

9. The curved balloon catheter retractor device of claim 1, wherein said pulling balloon is made of a material including a barium sulfate contrast agent so that it may be fully developed under X-rays to measure the specific location of the pulling balloon.

\* \* \* \* \*